(12) United States Patent
Elger et al.

(10) Patent No.: US 7,053,077 B1
(45) Date of Patent: May 30, 2006

(54) USE OF BIOGENIC ESTROGEN SULFAMATES FOR HORMONE REPLACEMENT THERAPY

(75) Inventors: Walter Elger, Berlin (DE); Pekka Lähteenmäki, Turku (FI); Matti Lehtinen, Piispanristi (FI); Gudrun Reddersen, Jena (DE); Holger Zimmermann, Ilmenau-Roda (DE); Michael Oettel, Jena (DE); Sigfrid Schwarz, Jena (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/744,574

(22) PCT Filed: May 13, 1999

(86) PCT No.: PCT/DE99/01496

§ 371 (c)(1),
(2), (4) Date: Apr. 5, 2001

(87) PCT Pub. No.: WO00/06175

PCT Pub. Date: Feb. 10, 2000

(30) Foreign Application Priority Data

Jul. 28, 1998 (DE) .................................. 198 34 931

(51) Int. Cl.
*A61K 31/56* (2006.01)
(52) U.S. Cl. ..................... 514/177; 514/178; 514/182; 514/874
(58) Field of Classification Search ................ 514/310, 514/177, 178, 182
See application file for complete search history.

(56) References Cited

U.S. PATENT DOCUMENTS 5,314,694 A * 5/1994 Gale et al.
5,633,242 A 5/1997 Oettel

FOREIGN PATENT DOCUMENTS

WO 95 01161 1/1995
WO WO-96/05216- * 2/1996

OTHER PUBLICATIONS

Elger, W. et al.: "Sulfamates of various estrogens are prodrugs with increased systemic and reduces hepatic estrogenicity at oral application." *Journal of Steroid Biochemisty and Molecular Biology*, vol. 55, No. 3-4 pp. 395-403.
Elger, W et al. "Novel oestrogen sulfamates: a new approach to oral hormone therapy" vol. 7, No. 4, 1998 pp. 575-658.

* cited by examiner

*Primary Examiner*—Sreeni Padmanabhan
*Assistant Examiner*—Abigail M. Cotton
(74) *Attorney, Agent, or Firm*—Millen, White, Zelano & Branigan, P.C.

(57) ABSTRACT

The invention relates to the use of biogenic estrogen sulfamates for the oral discontinuous application for hormone replacement therapy (HRT). The discontinuous administration takes place in intervals ranging from 2 to 40 days. The invention also provides the additional application of gestagens, preferably continuously in the form of an implant or in the form of an intrauterine releasing system (IUD). Estrone sulfamate, estradiol sulfamate or an N-acyl sulfamate of estrone, estradiol or estriol having up to 7 C-atoms in the acyl chain, or a combination comprised of two or more of said active ingredients are used as biogenic estrogen sulfamates.

15 Claims, 6 Drawing Sheets

USE OF BIOGENIC ESTROGEN SULFAMATES FOR HORMONE REPLACEMENT THERAPY

CROSS-REFERENCE TO RELATED APPLICATIONS

Figure 1:
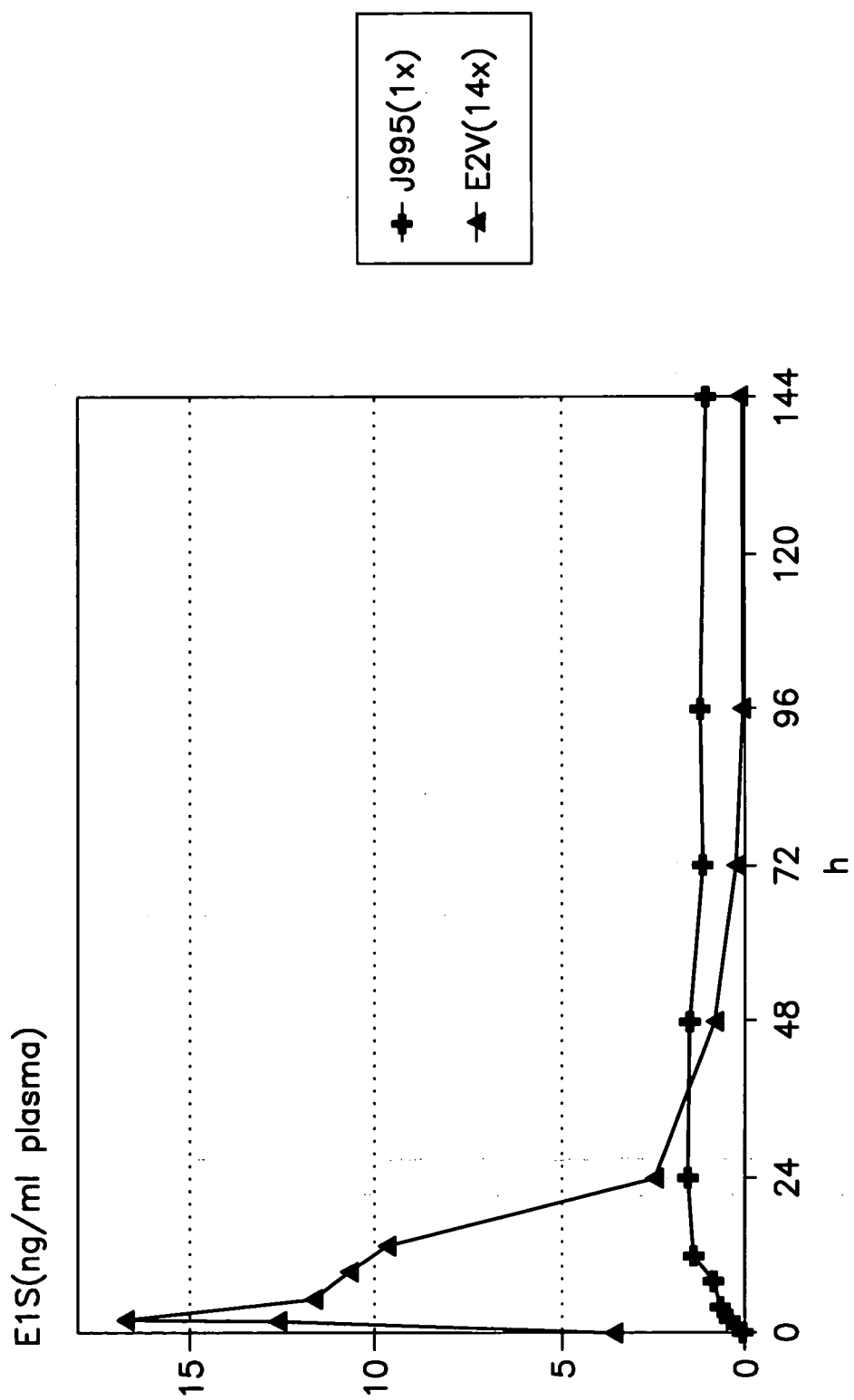

This application is a 371 of PCT/DE99/01496, filed May 13, 1999.

The invention relates to the use of biogenic estrogen sulfamates for oral, intermittent administration for hormone replacement therapy (HRT).

Estrogens are formed in the ovary predominantly by vesicular ovarian follicles and corpora lutea. In addition, many organs and tissues are able to generate estrogens, for example from androstenedione and dehydroepiandrosterone, which are secreted in substantial amounts by the adrenal glands of the human. Under certain circumstances, several enzymes, and at the end of the chain, ultimately the aromatase are involved in the corresponding conversion. Another method for development of estrogens in the tissue is the hydrolytic cleavage of conjugates of the natural estrogens, primarily that of the estrone sulfate. It has to be assumed that estrogens that are produced in the tissue locally play an important role in physiological and pathological processes. They are not able to prevent the estrogen deficiency in the overall organism, however, which occurs around age 50 upon the cessation of the ovarian function.

Estrogens play an essential role in hormonal contraception and in the menopausal hormone replacement therapy (HRT) as well as in the treatment of gynecological (e.g., breast cancer) and andrological (e.g., prostate cancer) clinical pictures. In the case of contraception, estrogens are required one time to suppress follicular maturation and ovulation reliably; on the other hand they then substitute the largely suppressed endogenic, ovarian secretion of estradiol. This substitution is essential for preserving an artificial menstrual cycle and other functions of the sexual organs, which is not accomplished satisfactorily with a gestagen by itself. In addition, endogenic and exogenic estrogens have important central nervous and metabolic functions in the female organism. Normal estrogen levels decisively contribute to well-being. Its presence counteracts the development of cardiovascular diseases by various mechanisms: production of "advantageous" lipoprotein patterns in the blood, inhibition of lipid retention in the vascular wall, lowering of the blood pressure by advantageous influencing of vasotonia, reduction of perfusion resistance in important vascular zones, attenuation of contractile stimuli on vascular muscle. Under the action of estrogens, the vascular inner walls release factors that counteract the development of blood clots. In women, estrogens are essential for preserving the bone structure. Its loss can produce the development of bone destruction (osteoporosis). The last-mentioned "central nervous" and "metabolic" effects of estrogens are essential considerations of HRT.

In all positive aspects of estrogen therapy, there are unsolved problems that limit the therapeutic use of estrogens or contain undesirable actions; the latter are discussed in the following chapters with respect to the subject of the invention.

Natural estrogens (estradiol, estrone, estrone sulfate, esters of estradiol, estriol) are bio-available to only a very small extent when administered orally. This proportion is individually variable, such that general dose recommendations are not possible. The estrogen dose in the HRT must very often be matched individually. The quick elimination of substances from the blood is also problematical in nature. Even in cases where an oral preparation is given daily, the active ingredient and its relevant metabolites are eliminated to a large extent between two intakes, so that it cannot be assumed that the latter does not result in a disruption of the estrogenic action. In studies by Kuhnz et al. (Kuhnz, W.; Gansau, C.; Mahler, M.: "Pharmacokinetics of Estradiol, Free and Total Estrone, in Young Women. Following Single Intravenous and Oral Administration of 17βEstradiol," Arzneim.-Forsch./Drug Res. 43 (2), 9, 966–973 (1993)), it was found that the estradiol and estrone values 24 hours after administration of different doses of estradiol (2, 4 and 8 mg as a one-time administration) had dropped to less than 50% of the maximum level. This observation shows that dose increase is by no means able to eliminate the problem of strong fluctuations of the hormone level in the 24-hour cycle with daily intake. The relevance of this assumption can also be supported by other observations. In postmenopausal women, estriol was not osteoporectively effective even at very high oral dosages (Lindsay, R.; Hart, D. M.; Maclean, A.; Garwood, J.; Clark, A. C.; Kraszewski, A.: "Bone Loss During Estriol Therapy in Postmenopausal Women" Maturitas Jun 1 (4), 279–285 (1979)). In women, it has an especially short half-life of about 1.5–5.3 hours (Heithecker, R.; Aedo, A. R.; Landgren, B. M.; Cekan, S. Z.: "Plasma Estriol Levels after Intramuscular Injection of Estriol and Two of its Esters" Horm. Res. 35, 234–238 (1991)). It was demonstrated that this estrogen has a protective action in the bone after ovariectomy, if uniform active ingredient levels are maintained in the blood (Elger, W.; Schneider, B.; Oettel, M.; Ernst, M.; Hübler, D.; Dittgen, M.: "Use of Estradiol for Treatment of Menopausal Osteoporosis" Patent DE-A 42 09 295).

In recent years, transdermal therapy processes were developed. The processes reduce the fluctuations of the estrogen levels in the blood, but cannot quite avoid the latter. The essential drawback of this administration technology presumably lies in the complicated use in comparison to simple oral administration. Oral preparations still predominate on the HRT market despite their discussed drawbacks. Transdermal forms of administration are abandoned by their users, moreover, on average earlier than is the case for oral preparations.

The latter are rejected by medical science, citing their metabolic effects for the field of application of HRT. The most important synthetically modified estrogenic steroid is ethinylestradiol (EE). This estrogen is dominant in oral hormonal contraception. In addition to EE, mestranol, which is a "prodrug," is used in a few products, and is metabolized into EE in the organism. In the case of oral administration (human), EE is much more bio-available than the above-mentioned natural estrogens, but the oral bio-availability individually varies in an extraordinarily great manner. Different authors have pointed out this fact and the partially irregular behavior of the blood level plots after this substance is administered orally (Goldzieher, J. W.: Pharmacology of Contraceptive Steroids: A Brief Review, "Am. f. Obstet. Gynaecol. 160, 1260–1264 (1989); Goldzieher, J. W.: "Selected Aspects of the Pharmacokinetics and Metabolism of Ethinyl Estrogens and their Clinical Implications" Am. J. Obstet. Gynaecol. 163, 318–322 (1990); Hümpel, M.; Täuber, U.; Kuhn, W.; Pfeffer, M.; Brill, K.; Heithekker, R.; Louton, T.; Steinberg, B.: "Comparison of Serum Ethinyl Estradiol, Sex-Hormone-Binding Globulin, Corticoid-Binding Globulin and Cortisol Levels in Women Using Two Low-Dose Combined Oral Contraceptives," Horm. Res. 33, 35–39 (1990); Kuhnz, W.; Louton T.; Back, D. J.; Michaelis, K: "Radioimmunological Analysis of Ethinylestradiol in Human Serum" Arzneim.-Forsch./Drug Res. 43 (1), No. 1, 16–21 (1993)).

In oral use, after resorption from the lumen of the bowels, active ingredient gets into the organism via the liver. For estrogen active ingredients, this fact is of special importance since the liver is a target organ for estrogens, and their oral administration and the associated passing through the liver results in strong estrogen effects in the liver.

I.a., the syntheses of transport proteins CBG, SHBG, TBG, the angiotensinogen, various factors that play an important role in the physiology of blood clotting and lipoproteins belong to the secretion activities of the human liver that are regulated by estrogens.

If the natural estrogens are fed to the female organism without passing through the liver, e.g., by transdermal administration, the above-mentioned liver functions remain practically unchanged. In the case of oral administration, therapeutically equivalent doses of natural estrogens result in significant reactions of hepatic parameters: increase of SHBG, CBG, angiotensinogen, HDL (high density lipoproteins). Considerably more strongly pronounced than in natural estrogens are corresponding hepatic estrogen effects in equine estrogen mixtures, so-called conjugated estrogens (Campbell, S.; Whitehead, M. I.: "Potency and Hepatocellular Effects of Estrogens after Oral, Percutaneous and Subcutaneous Administration" International Congress on the Menopause (3rd: Ostend, Belgium 1981), Workshop 12, 103–125 in The Controversial Climacteric/MTP Press Lancaster 1982, Editors Van Keep, P. A.; Utian, W. H., Vermeulen). Ethinyl-estradiol and OES have still stronger hepatic estrogeneity. Relative to anti-gonadotropic properties, the EE in the liver is about 4–18 times more strongly estrogenically active than orally administered natural estrogens (Campbell, S. et al. ibid.). A very disadvantageous dissociation of properties is thus present, since the desired systemic effects (effects in the genital tract, bones, central nervous system) are outweighed by the undesired hepatic effects.

In HRT and for contraception, estrogens are quite predominantly used in combination with a gestagen, e.g., levonorgestrel, desogestrel, norethisterone, medroxyprogesterone acetate, megestrol, cyproterone acetate, chlormadinone acetate, dienogest, or drospirenone. In the case of a contraceptive strategy, a synergism in the suppression of ovulation is achieved by the combination of estrogen and gestagen. A second important aspect of the combination of estrogen and gestagen is the conversion of the mucous membrane of the uterus, analogously to the processes that physiologically occur in the luteal phase of the normal cycle.

The interaction of both hormone types prevents excessive estrogen effects in this tissue, which, as has been proven, promote the development of endometrial carcinomas. Moreover, the endometrium is put into a state that results in "menstrual" bleeding after the treatment is discontinued.

In HRT, the decisive aspect of the combination with a gestagen is the inhibition of the proliferation action in the endometrium. The other interactions of this combination are unimportant or even problematical in nature for the achievement of the therapeutic goals. It is not disputed in medical science that in the case of predisposed women, the positive effect of an estrogen treatment can be strongly impaired by the combination with a gestagen (Breckwoldt et al.: "Consensus der Menopause Gesellschaft deutschsprachiger Länder [Consensus of the Menopause Society of German-speaking Countries]" in Menopause 6/Aesopus Verlag GmbH Basel 173–177 (1993), Editor Lauritzen, C.). The occurrence of depressive moods is an example of this. Possible negative effects of the combination in comparison to a pure estrogen therapy are subjects of prolonged controversies with respect to cardiovascular morbidity and mortality (Lobo, R. A.; Whitehead, M.: "Too Much of a Good Thing? Use of Progestogens in the Menopause: An International Consensus Statement" Fertility and Sterility 51, No. 2, Feb. 1989; Kuhl, H.: Hormonale Kontrazeption und Substitutionstherapie: Die Bedeutung des Gestagens für kardiovaskuläre Erkrankungen [Hormonal Contraception and Replacement Therapy: The Importance of Gestagen for Cardiovascular Diseases]" Geburts. u. Frauenheilk. [Obstetrics and Gynecology] 52, 653–662 (1992)). Another problem area is the effect of a combination of estrogen and gestagen on the promotion of latent breast cancers. In the mammary glands, progesterone plays a role in the structure of the glands in pregnancy. Accordingly, its role as a mitosis-triggering factor in this organ is in part regarded as somewhat similar to the role of estrogens in the uterus (Zumoff, B.: "Biological and Endocrinological Insights into the Possible Breast Cancer Risk from Menopausal Estrogen Replacement Therapy" Steroids 58, 196–204 (1993); Said, T. K.; Conneely, O. M.; Medina, D.; O'Maley, B. W.; Lydon, J. P.: Progesterone, in Addition to Estrogen, Induces Cyclin D1 Expression in the Murine Mammary Epithelial Cell, in Vivo Endocrinology 138, No. 9, p. 3933 (1997); by Schoultz, B.; Söderqvist, G.; Tani, E.; Skoog, L.: "Effects of Female Sex Steroids on Breast Tissue" European Journ. of Obstet. & Gynaecol. and Reproductive Biol. 49, p. 55 (1993)).

To avoid demonstrated drawbacks and above-mentioned uncertainties of gestagen use in HRT, new treatment strategies are necessary that aim at minimal or local gestagen treatment, whereby there can be no doubt as to the basic need to add gestagen.

The pharmacokinetics and pharmacodynamic weak points of natural and synthetic estrogens also have major clinical importance. In the case of estrogen therapy with high-dosed estrogens, thromboembolic diseases with a fatal outcome are a known complication. In the weakened form, this potential for side effects of conventional estrogens determines the strategy of oral hormonal contraception. With respect to the desired contraceptive effect, maintaining the monthly menstrual process, taking the potential for side effects into account is a delicate balancing act.

With today's technology, therapy with natural estrogens readily requires individual dose adjustments. Corresponding treatments are associated with great uncertainties and actually contain the risk of over- and under-dosing. Oral therapy is also demonstrably loaded with undesirable hepatic effects when natural estrogens (estradiol, estradiol valerate, estrone sulfate, so-called conjugated estrogens) are used. It has to be assumed, moreover, that the unphysiologically strong fluctuations of the blood level of the administered estrogens and their active metabolites have a negative effect for achieving the therapeutic targets. Actually, i.e., the conventional oral HRT remains behind its theoretical possibilities.

The transdermal HRT or other parenteral techniques (implants, injections) of the hormone administration avoid some of the drawbacks that are discussed for the oral HRT. They have the drawback, however, that they can be used only with the aid of a physician (injections, implants) or represent an increased burden in the way that they are used, which causes patients to abandon the therapy, so that the beneficial effect of HRT on health and quality of life is lost.

Known from WO-A 9501161 is a packaging for use in hormone replacement therapy, in which estrogen, especially estradiol, is administered in the form of a subdermal implant, together with a progestin, which is administered using an intrauterine release system. Such a packaging has the drawback that in any case the implant must be inserted by a physician.

The object of this invention is to overcome the drawbacks in the known hormone replacement therapy (HRT).

The object is achieved according to the invention by the use of biogenic estrogen sulfamates for oral, intermittent administration for hormone replacement therapy.

The object is also achieved according to the invention by the use of biogenic estrogen sulfamates for the production of pharmaceutical agents for oral, intermittent administration for hormone replacement therapy.

It is preferred according to the invention that the biogenic estrogen sulfamate be estrone sulfamate, estradiol sulfamate, estriol sulfamate or an N-acylsulfamate of estrone, estradiol or estriol with up to 7 C atoms in the acyl chain or a combination of two or more of the above-mentioned active ingredients. Especially preferred are N-acetyl and N-propionyl derivatives of sulfamates.

It is preferred according to the invention that the individual administrations have an interval of 2 to 40 days. Advantageously, in the use of estrogen sulfamates or their N-acyl derivatives according to the invention, in addition at least one gestagen is administered.

In this connection, preferred as gestagens according to the invention are levonorgestrel, desogestrel, norethisterone, medroxyprogesterone acetate, megestrol, cyproterone acetate, chlormadinone acetate, dienogest, drospirenone or a combination of two or more of the above-mentioned active ingredients.

In this case, it is especially preferred according to the invention that the gestagen be administered continuously in the form of an implant or in the form of an intrauterine release system (IUD) or in combination with the above-mentioned types of administration.

In the case of ovariectomized rats, a strong oral estrogenic action was observed after treatment with estradiol sulfamate. In comparison to estradiol in an equimolar dose, higher and prolonged blood levels of estradiol and estrone were noted after estradiol sulfamate (J995). These release-processes were ended after 24 hours. Even very high dosages of J995 did not result in an extension of the estrogen actions.

It was now found, surprisingly enough, that the release of the above-mentioned hormones in humans from the sulfamate prodrug proceeds much more slowly than in rats.

The period of estrogen release and hormone action could be affected by the level of the dose, surprisingly enough, without excessive active ingredient levels or effects having been noted.

Pharmacodynamically relevant blood levels were also measured 4 weeks after one-time administration.

With daily treatment at low dosages (100 µg of J995/day), completely uniform active ingredient levels (estradiol, estrone) could be built up and their biological relevance could be demonstrated.

It was found, surprisingly enough, that at comparable estrone and estradiol levels in the blood of women after oral treatment with estradiol valerate or estradiol sulfamate, the latter induces about 10 times lower levels of estrone sulfate. Since this estrogen metabolite is suspected of promoting the growth of latent breast cancers, the observation of lower levels of estrone sulfate is a surprising advantage compared to the conventional oral HRT. With respect to estrone sulfate increase, estradiol sulfamate and transdermal therapy behave comparably. This can be considered as a considerable improvement in oral therapy possibilities.

This invention has a number of advantages compared to the prior art. This invention improves conventional strategies of the HRT under all discussed problem areas of conventional HRT.

The compliance is increased. An HRT is demonstrated according to the invention that is as easy to use as oral HRT or even improved by the option of an intermittent therapy, for example by weekly or monthly intake intervals as an alternative to daily treatment.

The pharmacodynamics is also considerably improved by the use according to the invention. The release of estradiol or estrone from the sulfamate prodrug has the effect that hepatic estrogen action with therapeutic doses cannot be expected. This is an important step forward in comparison to conventional oral HRT.

The levels of estrone sulfate also remain far below those of conventional oral HRT. Estrone sulfate is cleaved from (latent) breast cancers by their high sulfatase activity. The danger of a promotion action by conventional oral HRT exists. This is reduced by this invention.

Also in reference to the pharmacokinetics, the use according to the invention has considerable advantages. By slow release from the sulfamate produg in humans according to the invention, very uniform, exactly defined levels of natural estrogens can be built up in the blood.

Slow release of natural estrogens, in connection with a high oral bio-availability of the steroid portion of the administered estradiol sulfamate according to the invention, allows use at larger intervals.

The period of hormone action can be controlled according to the invention by the amount of the dose. Very low dosages (20–300 µg) are optimum for 1- to 3-day treatment intervals; medium dosages (0.5–5.0 mg/day) are suitable according to the invention for 5- to 10-day treatment intervals; and higher dosages (2.0–20 mg/day) are suitable according to the invention for treatment intervals of 20–40 days.

Compliance with an additional gestagen treatment is also considerably improved. The HRT according to the invention is improved in its acceptance by gestagen treatments by means of IUDs or implants that continuously release the gestagenic active ingredients after one-time introduction by the physician for a prolonged time. The advantage of the convenience of an intermittent estrogen treatment is thus maintained according to the invention. In combination with conventional estrogen therapy, a corresponding advantage cannot be achieved.

The pharmacodynamics is also improved by the gestagen treatment according to the invention. The advantageous estrogen action for the HRT is not impaired by low systemic substance release (implant) or the limitation of the active ingredient release in the uterus. Problems that could follow from systemic gestagen effects are reduced to a minimum.

The sulfamates of the biogenic estrogens and their N-acyl derivatives are known in the art. The production of these compounds is carried out in a way that is known in the art by synthetic means from the biogenic estrogens. In this case, optionally a portion of the free OH groups or other reactive groups are provided with suitable protective groups, which are cleaved again after synthesis is completed. For the production of N-acyl derivatives of the sulfamates, the corresponding N-acylated amidosulfuric acid derivatives are used for synthesis.

The production of the pharmaceutical compositions that are necessary for use according to the invention is known per se to one skilled in the art. It corresponds to those as they are known, for example, for the production of oral agents for hormonal contraception.

The pharmaceutical agents of the invention are produced in a known way with the commonly used solid or liquid vehicles or diluents and the commonly used pharmaceutical-technical adjuvants corresponding to the desired type of administration at a suitable dosage. The preferred preparations consist in a form for dispensing that is suitable for oral administration. Such forms for dispensing are, for example, tablets, film tablets, coated tablets, capsules, pills, powders, solutions or suspensions or depot forms.

Corresponding tablets can be obtained by, for example, mixing the active ingredient with known adjuvants, for example inert diluents, such as dextrose, sugar, sorbitol, mannitol, polyvinylpyrrolidone, explosives such as corn starch or alginic acid, binders such as starch or gelatin, lubricants such as magnesium stearate or talc and/or agents for achieving a depot effect such as carboxylpolymethylene, carboxylmethyl cellulose, cellulose acetate phthalate or polyvinyl acetate. The tablets can also consist of several layers.

Coated tablets can accordingly be produced by coating cores produced analogously to the tablets with agents commonly used in tablet coatings, for example polyvinylpyrrolidone or shellac, gum arabic, talc, titanium dioxide or sugar. In this case, the shell of the coated tablet can also consist of several layers, whereby the adjuvants that are mentioned above in the tablets can be used.

The production of implants or intrauterine release systems (IUD) for the administration of gestagen are likewise known to one skilled in the art.

The following examples explain the invention:

In the examples below, the determination of the plasma levels of the estrogens with validated methods that are known and acknowledged in the art was performed.

EXAMPLE 1

Cf. Estradiol Valerate and Estradiol Sulfamate Relative to Induced Estrone Sulfate Levels in Postmenopausal Women (FIG. 1).

After one-time oral administration of 2 mg of estradiol valerate (EV) or 2 mg of estradiol sulfamate, the estrone sulfate levels in plasma increase. This increase turns out much stronger in the case of EV but also ends faster, so that 48 hours after administration, the estrone sulfate levels are higher after estradiol sulfamate than after EV.

EXAMPLE 2

Figure 2:
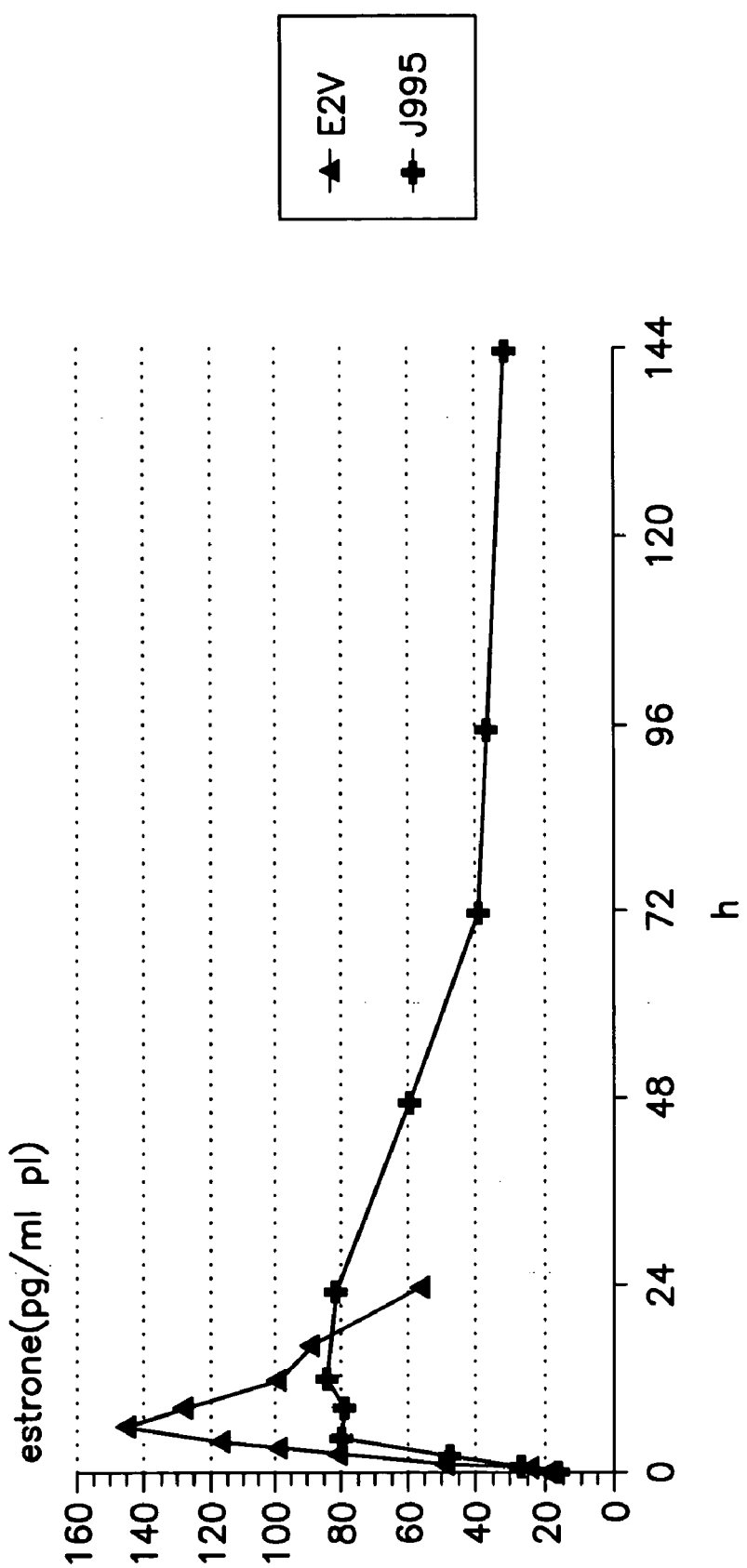

Cf. Estradiol Valerate and Estradiol Sulfamate Relative to Induced Estrone Levels in Postmenopausal Women (FIG. 2).

After one-time oral administration of 2 mg of estradiol valerate (EV) or 2 mg of estradiol sulfamate, the estrone levels in the plasma increase. This increase initially turns out stronger in the case of EV, but also ends faster. As early as 24 hours after administration, the estrone levels are higher after estradiol sulfamate than after EV. This increase persists for a long time.

EXAMPLE 3

Figure 3:
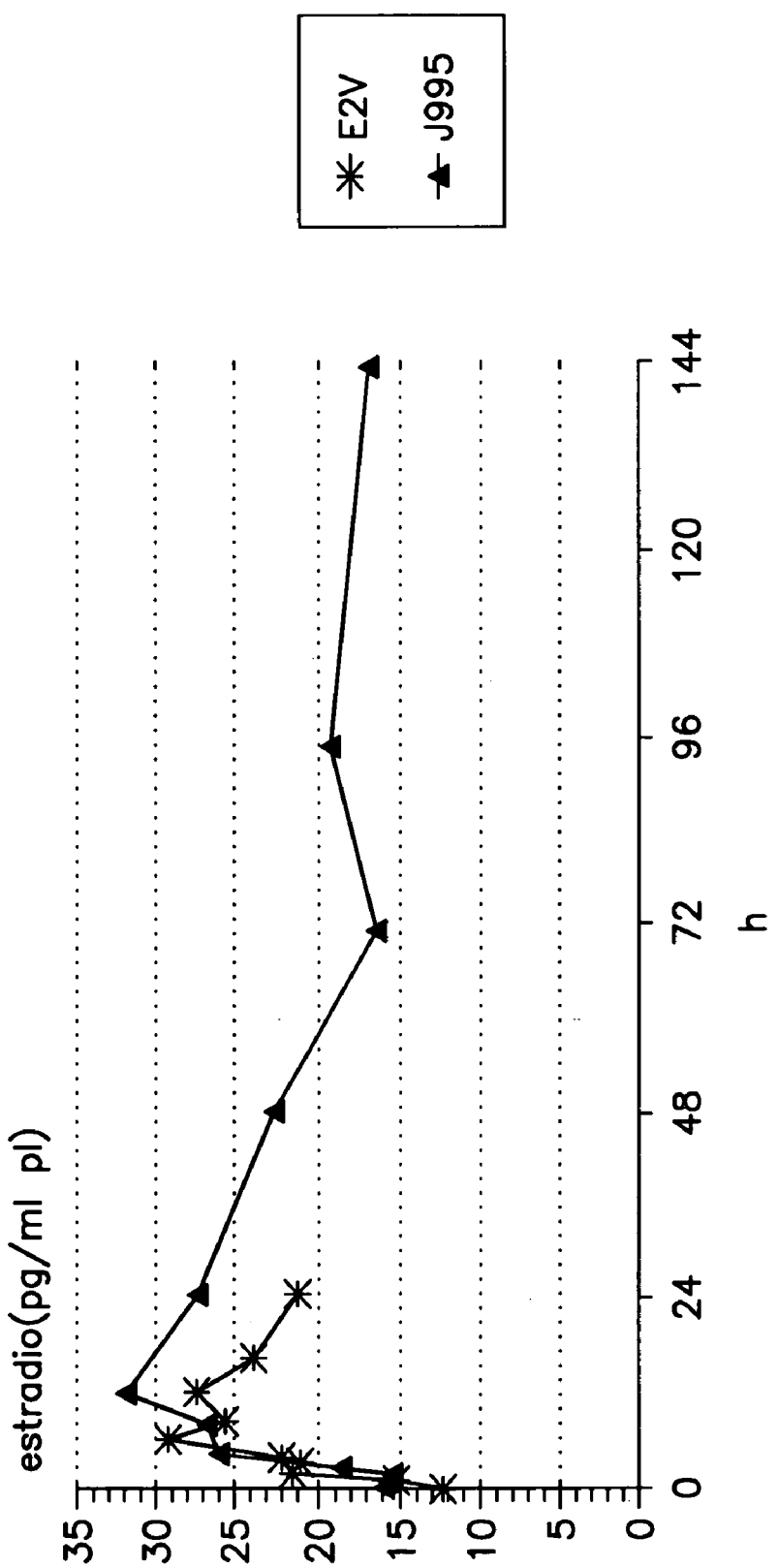

Cf. Estradiol Valerate and Estradiol Sulfamate Relative to Induced Estradiol Levels in Postmenopausal Women (FIG. 3).

After one-time oral administration of 2 mg of estradiol valerate (EV) or 2 mg of estradiol sulfamate, the estradiol levels in the plasma increase. This increase turns out weaker in the case of EV, and it also ends much faster. Even one week after treatment, estradiol blood levels that clearly exceed the starting values exist.

EXAMPLE 4

Figure 4:
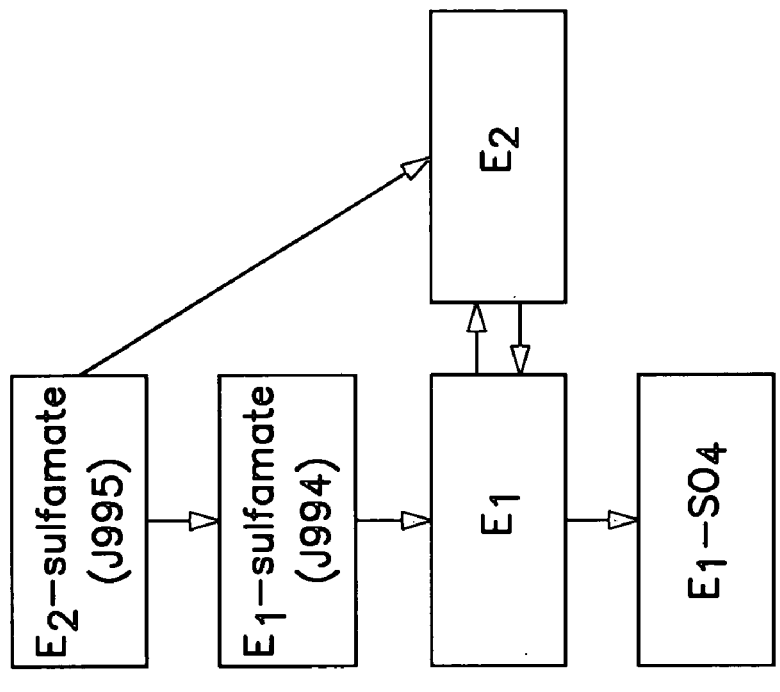
Figure 4:
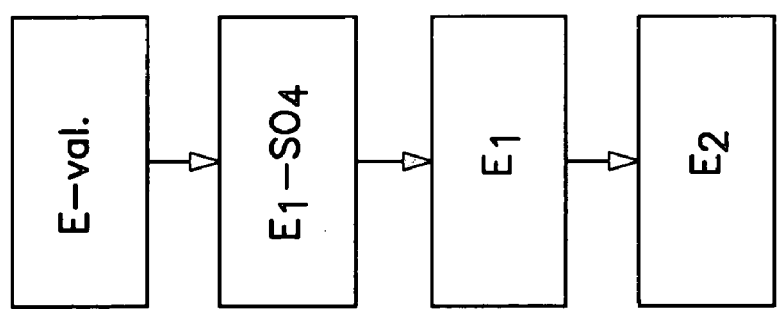

Mechanism of Generating Estrone and Estradiol According to Oral Use of Estradiol Valerate and Estradiol Sulfamate (FIG. 4).

A "pool" of estrone sulfate is produced in the blood by EV. From the latter is released estrone by hydrolysis, a small proportion of which is in turn metabolized into estradiol. The level of estrogen sulfate after estradiol sulfate that is very low in comparison to EV, but the altogether higher release (surface under the curve) of estrone after estradiol sulfamate confirms the direct conversion of the sulfamate into therapeutically relevant estrogens estrone and estradiol. Estrone sulfate is in this case only the main metabolite of the estrogens that are produced from the sulfamate.

EXAMPLE 5

Figure 5:
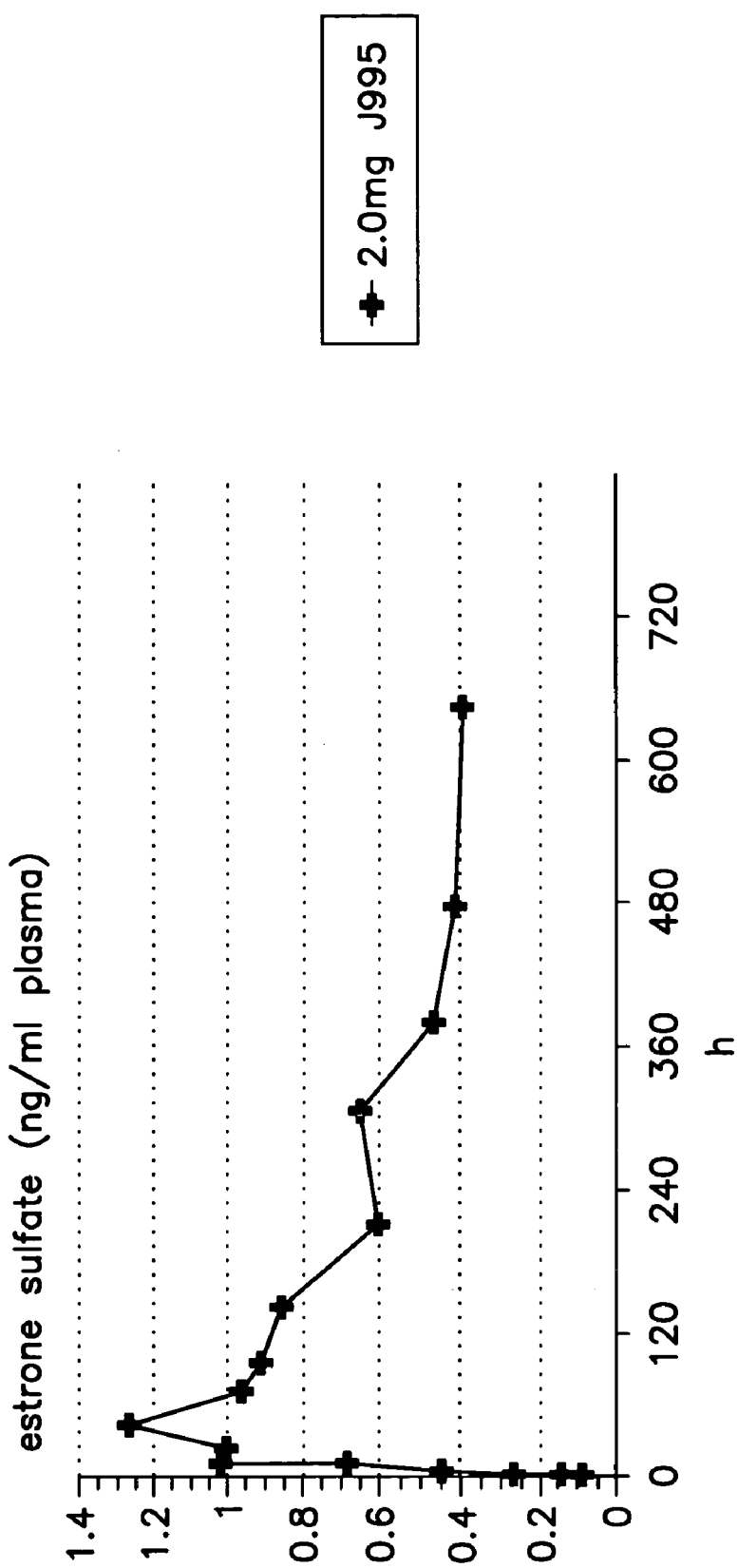

Period of the Estrogen Release from Estradiol Sulfamate Reflected by Elevated Estrone Sulfate Levels in Postmenopausal Women (FIG. 5).

The average estrone sulfate levels of three postmenopausal women show a clear increase compared to the starting values after a one-time administration of 2 mg over 600 hours.

EXAMPLE 6

Figure 6:
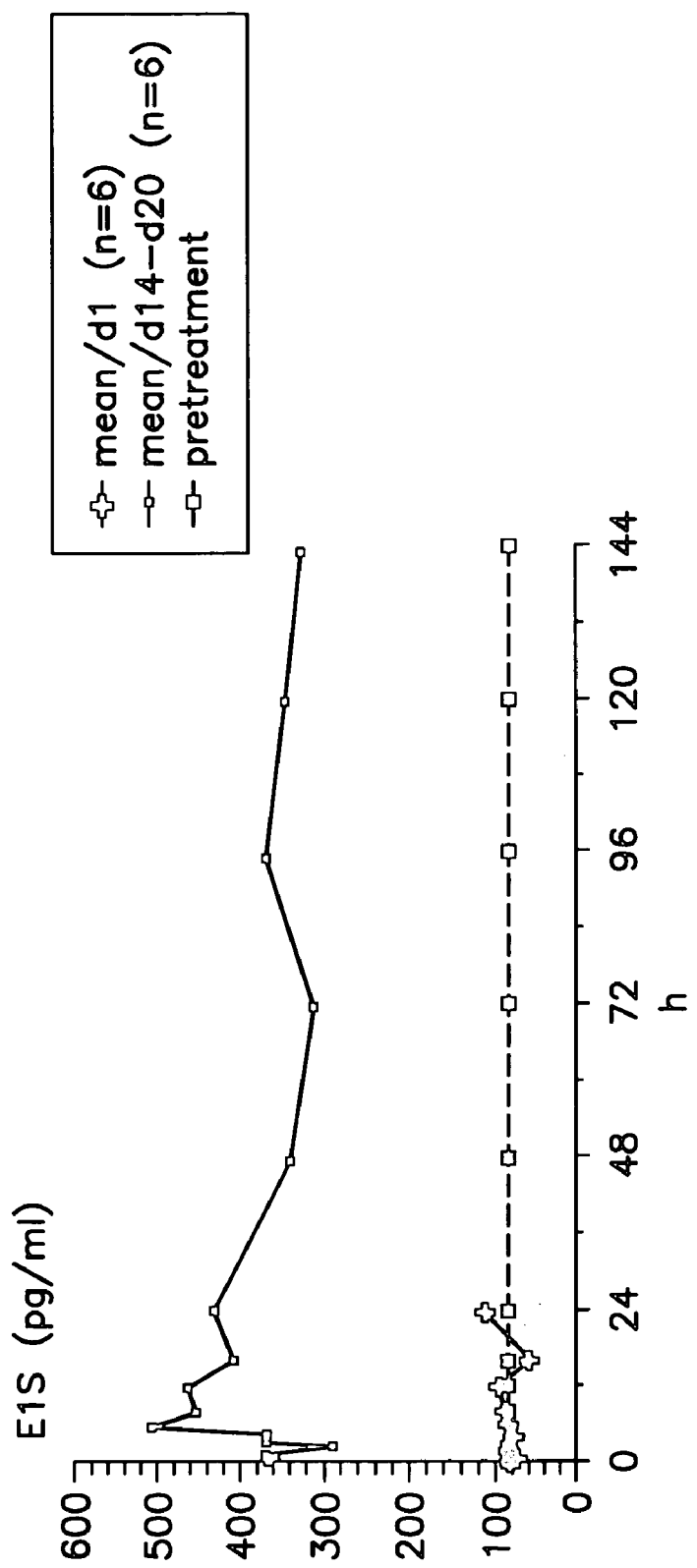

Estrogen Release from Estradiol Sulfamate Reflected by Elevated Estrone Sulfate Levels at Daily, Very Low Dosages in Postmenopausal Women (FIG. 6).

FIG. 6 shows the estrone sulfate level under daily administration of 0.1 mg of estradiol sulfamate. In the first 24 hours after the beginning of treatment, no clear increases are measured. At the end of the treatment, there are then clear increases. The last of 14 administrations resulted in a detectable increase of estrone sulfate in plasma; the latter had not yet disappeared even after six days. Relevant elevated estrone levels in the plasma were also measured in parallel. At the end of treatment, there was a considerable growth effect on the endometrium relative to the starting value.

The invention claimed is:

1. A method of achieving hormone replacement therapy in a woman comprising intermittently orally administering an estrogen sulfamate at a dosage of 0.5–5.0 mg on each day when administered in intervals of 5–10 days.

2. A method according to claim 1, wherein the estrogen sulfamate is estrone sulfamate, estradiol sulfamate, estriol sulfamate, N-acylsulfamate of estrone, estradiol or estriol having an acyl chain of up to 7 C atoms or mixtures thereof.

3. A method according to claim 1, further comprising the administration of a gestagen.

4. A method according to claim 3, wherein the at least one gestagen is levonorgestrel, desogestrel, norethisterone, medroxyprogesterone acetate, megestrol, cyproterone acetate, chlormadinone acetate, dienogest, drospirenone or a mixture thereof.

5. A method according to claim 3, wherein the at least one gestagen is continuously administered.

6. A method according to claim 5, wherein the continuous administration is in the form of an implant, in the form of an intrauterine release system or in the form of a combination thereof.

7. A method of achieving hormone replacement therapy in a woman comprising intermittently orally administering an estrogen sulfamate at a dosage of 2.0–20 mg on each day when administered in intervals of 20–40 days.

8. A method of achieving hormone replacement therapy in a woman comprising intermittently orally administering an estrogen sulfamate at a dosage of 20–300 µg/day in intervals of 2 or 3 days; 0.5–5.0 mg/day in intervals of 5–10 days; or 2.0–20 mg/day in intervals of 20–40 days.

9. A method according to claim 8, wherein the estrogen sulfamate is estrone sulfamate, estradiol sulfamate, estriol sulfamate, N-acylsulfamate of estrone, estradiol or estriol having an acyl chain of up to 7 C atoms or mixtures thereof.

10. A method according to claim 8, wherein the intermittent oral administration is carried out at an interval of 2 to 40 days between administrations.

11. A method according to claim 8, wherein the intermittent oral administration is carried out at an interval of 2 to 3 days between administrations.

12. A method according to claim 8, further comprising the administration of a gestagen.

13. A method according to claim 12, wherein the at least one gestagen is levonorgestrel, desogestrel, norethisterone, medroxyprogesterone acetate, megestrol, cyproterone acetate, chlormadinone acetate, dienogest, drospirenone or a mixture thereof.

14. A method according to claim 12, wherein the at least one gestagen is continuously administered.

15. A method according to claim 14, wherein the continuous administration is in the form of an implant, in the form of an intrauterine release system or in the form of a combination thereof.

* * * * *